United States Patent
Hartley et al.

(10) Patent No.: US 7,336,996 B2
(45) Date of Patent: Feb. 26, 2008

(54) RATE REGULARIZATION OF CARDIAC PACING FOR DISORDERED BREATHING THERAPY

(75) Inventors: Jesse W. Hartley, Lino Lakes, MN (US); Kent Lee, Fridley, MN (US); Jeffrey E. Stahmann, Ramsey, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 323 days.

(21) Appl. No.: 10/798,794

(22) Filed: Mar. 11, 2004

(65) Prior Publication Data

US 2005/0065566 A1    Mar. 24, 2005

Related U.S. Application Data

(60) Provisional application No. 60/504,382, filed on Sep. 18, 2003.

(51) Int. Cl.
    A61N 1/00    (2006.01)
(52) U.S. Cl. ....................................... 607/17
(58) Field of Classification Search .............. 607/9, 607/14, 17, 18, 20, 25; 600/513, 529, 533, 600/534, 536, 538
    See application file for complete search history.

(56) References Cited

U.S. PATENT DOCUMENTS

| | | | |
|---|---|---|---|
| 4,365,636 A | 12/1982 | Barker | |
| 4,813,427 A | 3/1989 | Schlaefke et al. | |
| 4,827,935 A | 5/1989 | Geddes et al. | |
| 4,830,008 A | 5/1989 | Meer | |
| 4,856,524 A * | 8/1989 | Baker, Jr. | 607/17 |
| 4,972,842 A * | 11/1990 | Korten et al. | 600/529 |
| 5,010,888 A * | 4/1991 | Jadvar et al. | 600/509 |
| 5,024,222 A | 6/1991 | Thacker | |
| 5,105,354 A | 4/1992 | Nishimura | |
| 5,123,425 A | 6/1992 | Shannon, Jr. et al. | |
| 5,146,918 A | 9/1992 | Kallok et al. | |
| 5,178,156 A | 1/1993 | Takishima et al. | |
| 5,187,657 A | 2/1993 | Forbes | |
| 5,211,173 A | 5/1993 | Kallok et al. | |
| 5,215,082 A | 6/1993 | Kallok et al. | |
| 5,233,983 A | 8/1993 | Markowitz | |

(Continued)

FOREIGN PATENT DOCUMENTS

EP    0750920    1/1997

(Continued)

OTHER PUBLICATIONS

Balaban et al., *Feasibility of Screening for Sleep Apnea Using Pacemaker Impedance Sensor*, NASPE (2001). Abstract Only.

(Continued)

*Primary Examiner*—Carl Layno
*Assistant Examiner*—Jon-Eric Morales
(74) *Attorney, Agent, or Firm*—Hollingsworth & Funk, LLC

(57) ABSTRACT

An approach to providing disordered breathing therapy includes providing cardiac overdrive pacing using rate regularization. Overdrive pacing therapy may be initiated following detection or prediction of disordered breathing. Characteristics of the disordered breathing or other patient conditions may be used to modify the pacing therapy.

36 Claims, 12 Drawing Sheets

U.S. PATENT DOCUMENTS

| | | |
|---|---|---|
| 5,335,657 A | 8/1994 | Terry, Jr. et al. |
| 5,466,245 A | 11/1995 | Heemels et al. |
| 5,483,969 A | 1/1996 | Testerman et al. |
| 5,485,851 A | 1/1996 | Erickson |
| 5,522,862 A | 6/1996 | Testerman et al. |
| 5,549,655 A | 8/1996 | Erickson |
| 5,622,178 A * | 4/1997 | Gilham .................... 600/523 |
| 5,645,570 A | 7/1997 | Corbucci |
| 5,713,933 A | 2/1998 | Greeninger |
| 5,738,102 A | 4/1998 | Lemelson |
| 5,792,188 A * | 8/1998 | Starkweather et al. .......... 607/5 |
| 5,802,188 A | 9/1998 | Starkweather et al. |
| 5,814,087 A | 9/1998 | Renirie |
| 5,844,680 A | 12/1998 | Sperling |
| 5,861,011 A | 1/1999 | Stoop |
| 5,891,023 A | 4/1999 | Lynn |
| 5,911,218 A | 6/1999 | DiMarco |
| 5,944,680 A | 8/1999 | Christopherson et al. |
| 5,974,340 A | 10/1999 | Kadhiresan |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,120,441 A | 9/2000 | Griebel |
| 6,126,611 A * | 10/2000 | Bourgeois et al. .......... 600/529 |
| 6,128,534 A | 10/2000 | Park et al. |
| 6,132,384 A | 10/2000 | Christopherson et al. |
| 6,141,590 A | 10/2000 | Renirie et al. |
| 6,161,042 A | 12/2000 | Hartley et al. |
| 6,240,316 B1 | 5/2001 | Richmond et al. |
| 6,251,126 B1 | 6/2001 | Ottenhoff et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,276,727 B1 | 8/2001 | Hopper et al. |
| 6,285,907 B1 | 9/2001 | Kramer et al. |
| 6,312,378 B1 | 11/2001 | Bardy |
| 6,336,903 B1 | 1/2002 | Bardy |
| 6,351,669 B1 | 2/2002 | Hartley et al. |
| 6,353,759 B1 | 3/2002 | Hartley et al. |
| 6,363,270 B1 | 3/2002 | Colla et al. |
| 6,398,728 B1 | 6/2002 | Bardy |
| 6,415,183 B1 * | 7/2002 | Scheiner et al. .............. 607/42 |
| 6,463,326 B1 | 10/2002 | Hartley et al. |
| 6,480,733 B1 | 11/2002 | Turcott |
| 6,574,507 B1 * | 6/2003 | Bonnet ........................ 607/20 |
| 6,589,188 B1 | 7/2003 | Street et al. |
| 6,641,542 B2 * | 11/2003 | Cho et al. .................... 600/529 |
| 6,752,765 B1 | 6/2004 | Jensen et al. |
| 6,752,766 B2 | 6/2004 | Kowallik et al. |
| 6,773,404 B2 | 8/2004 | Poezevera et al. |
| 6,810,287 B2 | 10/2004 | Zhu et al. |
| 6,881,192 B1 | 4/2005 | Park |
| 6,904,320 B2 * | 6/2005 | Park et al. .................... 607/17 |
| 6,928,324 B2 | 8/2005 | Park et al. |
| 6,988,498 B2 * | 1/2006 | Berthon-Jones et al. .................... 128/204.23 |
| 7,025,729 B2 * | 4/2006 | de Chazal et al. .......... 600/508 |
| 2002/0082652 A1 * | 6/2002 | Wentkowski et al. .......... 607/9 |
| 2002/0193697 A1 | 12/2002 | Cho et al. |
| 2002/0193839 A1 | 12/2002 | Cho et al. |
| 2003/0023184 A1 | 1/2003 | Pitts-Crick et al. |
| 2003/0055348 A1 * | 3/2003 | Chazal et al. ................ 600/509 |
| 2003/0055461 A1 | 3/2003 | Girouard et al. |
| 2003/0100925 A1 | 5/2003 | Pape et al. |
| 2003/0153953 A1 | 8/2003 | Park et al. |
| 2003/0153954 A1 * | 8/2003 | Park et al. .................... 607/17 |
| 2003/0153955 A1 * | 8/2003 | Park et al. .................... 607/17 |
| 2003/0153956 A1 | 8/2003 | Park et al. |
| 2003/0163059 A1 | 8/2003 | Poezevera et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2004/0002742 A1 | 1/2004 | Florio |
| 2004/0030362 A1 | 2/2004 | Hill et al. |
| 2004/0088027 A1 | 5/2004 | Burnes et al. |
| 2004/0138719 A1 * | 7/2004 | Cho et al. ..................... 607/42 |
| 2004/0176809 A1 | 9/2004 | Cho et al. |
| 2005/0039745 A1 * | 2/2005 | Stahmann et al. ..... 128/204.18 |
| 2005/0042589 A1 | 2/2005 | Hatlestad et al. |
| 2005/0043644 A1 | 2/2005 | Stahmann et al. |

FOREIGN PATENT DOCUMENTS

| | | |
|---|---|---|
| EP | 0770407 | 5/1997 |
| EP | 0 940 155 A | 9/1999 |
| EP | 1 151 718 A | 11/2001 |
| EP | 1 172 125 A1 | 1/2002 |
| EP | 1317943 | 11/2003 |
| WO | 8402080 | 7/1984 |
| WO | 9203983 | 3/1992 |
| WO | 99/04841 | 2/1999 |
| WO | WO 00/01438 A | 1/2000 |
| WO | WO 00/17615 | 3/2000 |
| WO | 02/087696 | 7/2002 |

OTHER PUBLICATIONS

Garrigue et al., Night Atrial Overdrive with DDD Pacing Results in a Significant Reduction of Sleep Apnea Episodes and QOL Improvement in Heart Failure Patients, NASPE (2001). Abstract Only.

Jais et al., Night Atrial Overdrive with DDD Pacing: a New Therapy for Sleep Apnea Syndrome, NASPE (2000). Abstract Only.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N.E. 158-175 (1997).

Bradley et al., Pathophysiologic and Therapeutic Implications of Sleep Apnea in Congestive Heart Failure, 3 J. Cardiac Failure 223-240 (1996). Abstract only.

Bradley et al., Sleep Apnea and Heart Failure, Park I: Obstructive Sleep Apnea, 107 Circulation 1671-1678 (2003).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Javaheri et al., Sleep Apnea in 81 Ambulatory Male Patients with Stable Heart Failure: Types and Their Prevalences, Consequences, and Presentations, 97 Circulation 2154-2159 (1998).

Olusola et al., Nightcap: Laboratory and home-based evaluation of a portable sleep monitor, 32 Psychophysiology, 32-98 (1995). Abstract only.

Roche et al., Screening of Obstructive Sleep Apnea Syndrome by Heart Rate Variability Analysis, 100 Circulation 1411-1455 (1999).

Shahrokh, A Mechanism of Central Sleep Apnea In Patients With Heart Failure, 341 N. Engl. J. Med. 949-954 (1999). Abstract only.

Vanninen et al., Cardiac Sympathovagal Balance During Sleep Apnea Episodes, 16 Clin. Physiol. 209-216 (1996). Abstract only.

Waldemark et al., Detection of Apnea using Short Window FFT Technique and Artifical Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993). Abstract only.

* cited by examiner

RATE REGULARIZATION OF CARDIAC PACING FOR DISORDERED BREATHING THERAPY

RELATED PATENT DOCUMENTS

This application claims the benefit of Provisional Patent Application Ser. No. 60/504,382, filed on Sep. 18, 2003, entitled "OVERDRIVE PACING THERAPY FOR DISORDERED BREATHING," to which priority is claimed pursuant to 35 U.S.C. §119(e) and which is hereby incorporated herein by reference in its entirety.

FIELD OF THE INVENTION

The present invention relates generally to providing cardiac pacing therapy for disordered breathing.

BACKGROUND OF THE INVENTION

Disordered breathing refers to a wide spectrum of respiratory conditions that involve disruption of the normal respiratory cycle. Although disordered breathing typically occurs during sleep, the condition may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes breathing. Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

SUMMARY OF THE INVENTION

Various embodiments of present invention involve methods and systems for providing disordered breathing therapy. One embodiment of the invention provides a method for delivering disordered breathing therapy. Cardiac intervals between cardiac beats are obtained. A first indicated pacing interval is determined based at least on a cardiac interval duration and a previous value of the first indicated pacing interval. Cardiac pacing to mitigate disordered breathing is provided based on the first indicated pacing interval.

Another embodiment of the invention involves a system for delivering disordered breathing therapy. The system includes a sensing circuit configured to sense cardiac beats. A controller is coupled to the sensing circuit. The controller is configured to determine a first indicated pacing interval based at least on a cardiac interval duration and a previous value of the first indicated pacing interval. A cardiac pacing circuit coupled to the controller is configured to provide cardiac pacing to mitigate disordered breathing based on the first indicated pacing interval.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
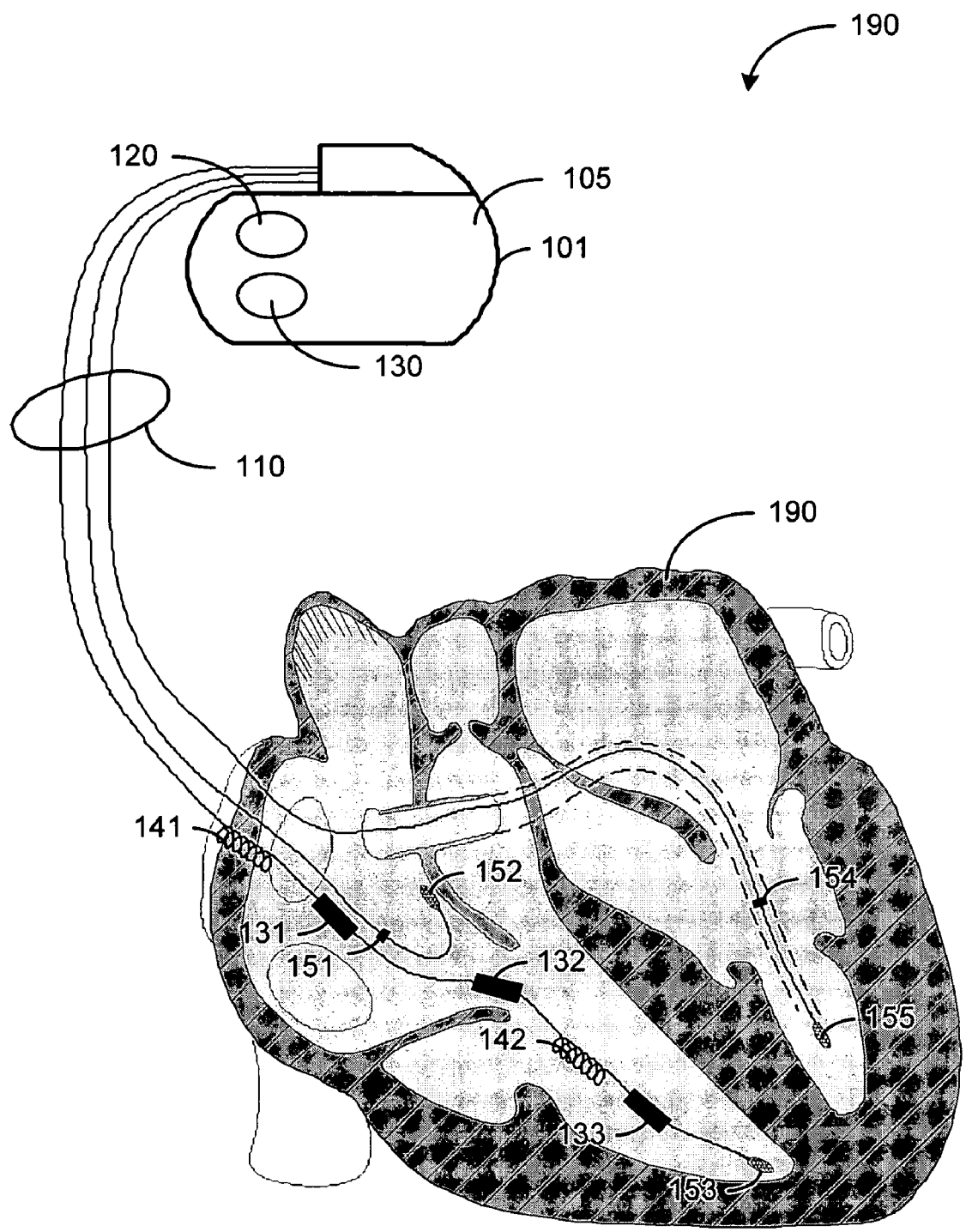
FIG. 1 is a partial view of an implantable medical device that may be used for coordinated patient monitoring, diagnosis, and/or therapy in accordance with an embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

A significant percentage of patients between the ages of 30 and 60 years experience some symptoms of disordered breathing. Although disordered breathing may occur while the patient is awake, it more often occurs during sleep. Sleep disordered breathing is associated with excessive daytime sleepiness, systemic hypertension, increased risk of stroke, angina and myocardial infarction. Disordered breathing is particularly prevalent among congestive heart failure patients, and may contribute to the progression of heart failure.

Various therapies have been used to treat central and/or obstructive disordered breathing episodes. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing apnea.

Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal (HG) nerve innervates the protrusor and retractor tongue muscles. An appropriately applied electrical stimulation to the hypoglossal nerve, for example, prevents backward movement of the tongue, thus preventing the tongue from obstructing the airway.

Cardiac stimulation may be used as a therapy for disordered breathing. Therapy methods for disordered breathing based on cardiac electrical stimulation are described in commonly owned U.S. patent application Ser. No. 10/643, 203, filed on Aug. 18, 2003, and U.S. patent application Ser. No. 10/643,154, filed on Aug. 18, 2003 both of which are incorporated by reference herein. Cardiac electrical stimulation therapy for disordered breathing may comprise an adaptive therapy. Such a therapy may be adapted, for example, to achieve an overall level of therapy efficacy, patient comfort, sleep quality, to prevent interaction with other patient therapies, or to prolong device service life, among other factors.

Overdrive pacing comprises pacing one or more heart chambers at a rate higher than an intrinsic rate. In accordance with embodiments of the invention, therapy to mitigate disordered breathing involves overdrive cardiac pacing of one or more atria and/or one or more ventricles as treatment for disordered breathing.

When operating in the overdrive pacing mode, a cardiac rhythm management device may deliver pacing pulses at a pacing preference (PP) rate that is a small amount above the intrinsic heart rate. If intrinsic beats are detected, the PP rate may be increased until it becomes slightly faster than the intrinsic heart rate of the sensed beat. The PP rate may then be gradually decreased to search for the intrinsic heart rate. After an intrinsic beat is sensed, the PP rate may be increased until the pacing rate is a small amount above the intrinsic heart rate.

In one implementation, a CRM device may be switched to operate in the overdrive pacing mode upon detection or prediction of disordered breathing. In another implementation, the CRM device may be switched to operate in the overdrive pacing mode following a determination that the patient is asleep. In yet another implementation, characteristics of the disordered breathing are used to develop an indicated pacing interval. The description that follows involves atrial overdrive pacing in the AAI(R) or DDD(R) modes. It will be appreciated that similar techniques may be implemented to effect ventricular overdrive pacing in the VVI(R) mode or overdrive pacing in a biventricular mode.

FIG. 1 is a partial view of an implantable medical device that may be used to implement overdrive cardiac pacing for disordered breathing therapy in accordance with embodiments of the invention. The implantable device illustrated in FIG. 1 represents a cardiac rhythm management device (CRM) 100 that includes an implantable pulse generator 105 electrically and physically coupled to an intracardiac lead system 110. Portions of the intracardiac lead system 110 are inserted into the patient's heart 190. In the illustrated embodiment, the intracardiac lead system 110 includes one or more electrodes 141-142, 151-155 configured to sense electrical cardiac activity of the heart and/or provide electrical stimulation to the heart. Portions of the housing 101 of the pulse generator 105 may optionally serve as a can electrode.

Communications circuitry is disposed within the housing 101 for facilitating communication between the pulse generator 105 and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors, patient-input devices and/or information systems.

The lead system 110 of the CRM 100 may incorporate a transthoracic impedance sensing system that may be used to sense the patient's respiration. The transthoracic impedance sensing system may include, for example, one or more intracardiac impedance electrodes 131-133 positioned in one or more chambers of the heart 190 and impedance drive/sense circuitry 130 within the housing of the pulse generator 105.

Various methods and systems for implementing impedance measurements in a cardiac rhythm management device are described in commonly owned U.S. Pat. Nos. 6,463,326, 6,161,042, 6,076,015 which are incorporated herein by reference.

In one implementation, impedance driver circuitry 130 induces a current that flows through the blood between an impedance drive electrode 133 and a can electrode on the housing 101 of the pulse generator 105. The voltage at the impedance sense electrodes 131, 132 relative to the can electrode changes as the patient's transthoracic impedance changes. The voltage signal developed between the impedance sense electrode 131, 132 and the can electrode is detected by the impedance sense circuitry 130.

Figure 2:
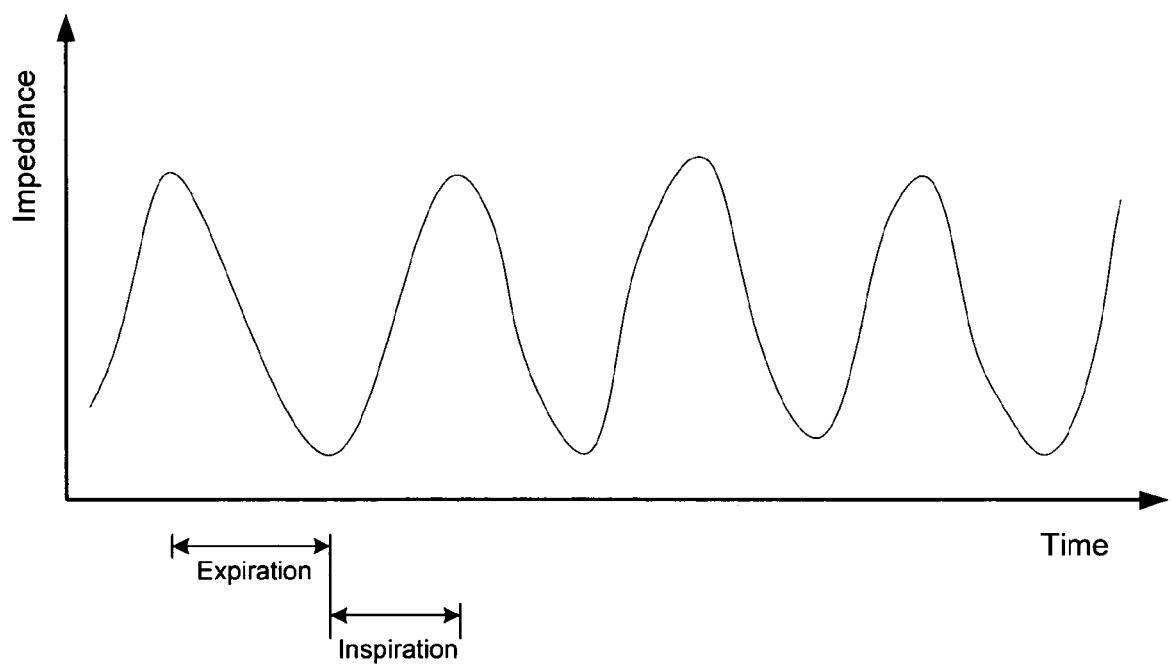
FIG. 2 is a graph of a respiration signal measured by a transthoracic impedance sensor that may be utilized in connection with providing cardiac pacing therapy for disordered breathing in accordance with embodiments of the invention.

The voltage signal developed at the impedance sense electrode, 131, 132 illustrated in FIG. 2, is proportional to the patient's transthoracic impedance. Transthoracic impedance increases during respiratory inspiration and decreases during respiratory expiration. The peak-to-peak transition of the impedance, illustrated in FIG. 2, is proportional to the amount of air moved in one breath, denoted the tidal volume. The amount of air moved per minute is denoted the minute ventilation.

In one embodiment, the patient's transthoracic impedance may be used to detect and/or predict disordered breathing episodes. Other patient conditions may alternatively or additionally be used for disordered breathing detection and/or prediction. The patient conditions may be acquired through the use of patient internal sensors, patient-external sensors, patient-input devices, and/or other information systems including network-based systems. The sensors, devices, and systems used to acquire patient condition information may be incorporated into the CRM device, or may be located remote from the CRM device. Communication between the CRM device and the sensors, devices, and systems used to acquire patient condition information may be accomplished through a wired connection, or through a wireless link such as a Bluetooth or proprietary wireless communications link.

Methods and systems for detecting and predicting disordered breathing are described in commonly owned U.S. patent application Ser. No. 10/309,770, filed Dec. 4, 2002 and commonly owned U.S. patent application Ser. No. 10/643,016, filed Aug. 18, 2003, both of which are incorporated herein by reference.

As previously discussed, the lead system 110 of the CRM 100 may include one or more pace/sense electrodes 141, 142, 151-155 positioned in one or more heart chambers for sensing electrical signals from the patient's heart 190 and/or delivering pacing pulses to the heart 190. The sense/pace electrodes 151-155 may be used to sense and/or pace one or more chambers of the heart, including the left ventricle, the right ventricle, the left atrium and/or the right atrium. The lead system 110 may include one or more defibrillation electrodes 141, 142 for delivering defibrillation/cardioversion shocks to the heart.

The pulse generator 105 may include circuitry for detecting cardiac arrhythmias and for providing therapy in the form of electrical stimulation delivered to the heart through the lead system 110. The pulse generator 105 may also include a disordered breathing processor 130 for detecting and/or predicting disordered breathing in accordance with embodiments of the invention.

Figure 3:
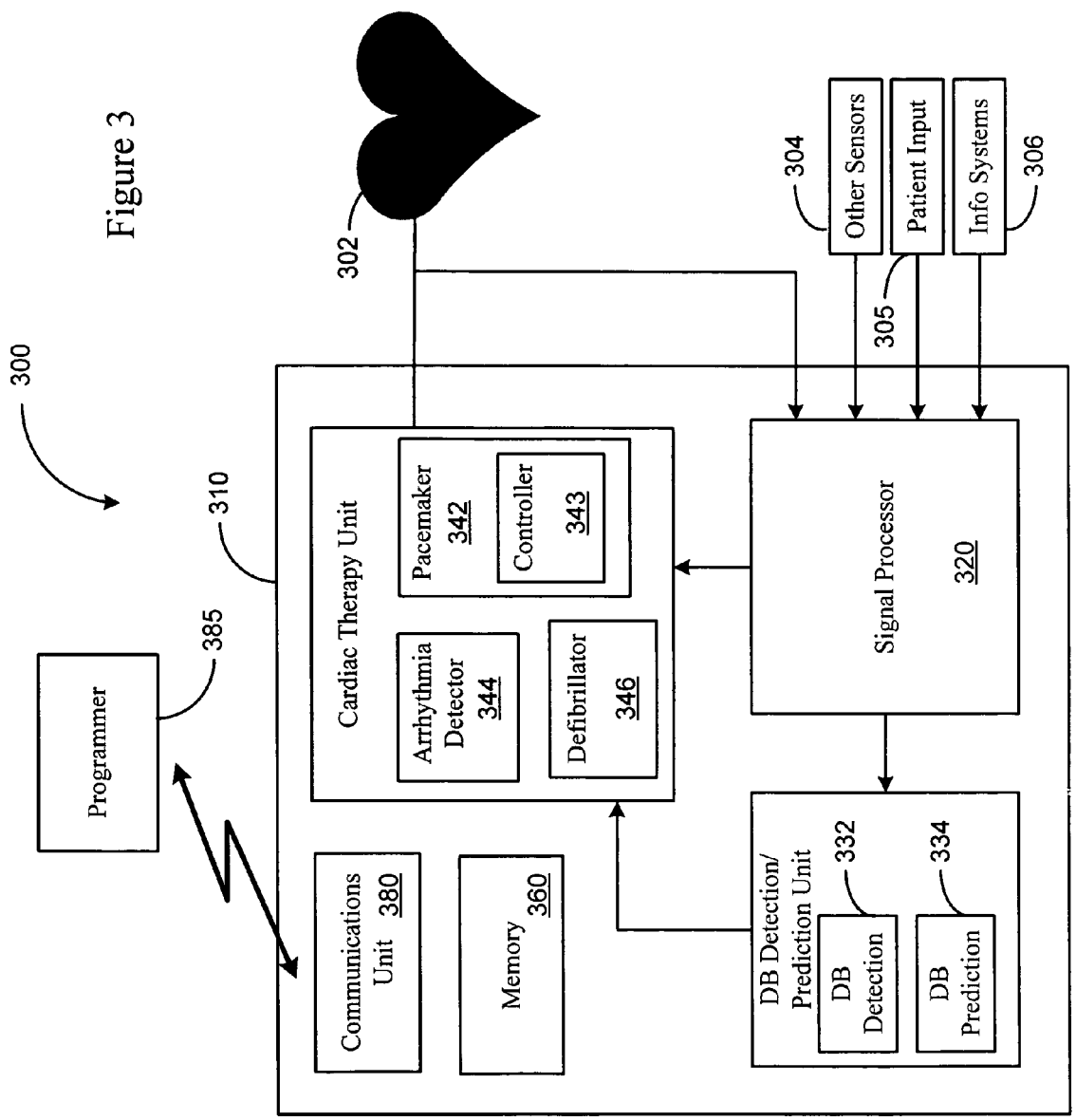
FIG. 3 is a block diagram of a medical system that may be used to provide cardiac pacing therapy for treating disordered breathing in accordance with embodiments of the invention.

FIG. 3 is a block diagram of a CRM 300 that may be used to provide cardiac pacing for disordered breathing therapy in accordance with embodiments of the invention. The CRM 300 may represent various types of cardiac rhythm management devices, including pacemakers, defibrillators, cardioverters, bi-ventricular pacemakers, and/or cardiac resynchronization devices, among others. Various components of the CRM 300 may be enclosed within a housing 310 that may be implanted or positioned external to the patient.

The CRM 300 includes electrodes 302 electrically coupled to the heart for sensing electrical activity of the heart and/or delivering electrical stimulation energy to the heart. The cardiac electrodes 302 may sense and/or pace one or more of the right atrium, left atrium, right ventricle, and left ventricle.

The CRM 300 may acquire information about conditions affecting the patient from the cardiac electrodes 302, the one or more sensors 304, patient input devices 305, and/or information systems 306. The patient conditions may be used to detect disordered breathing, predict disordered breathing, detect sleep, determine therapy interactions, determine therapy effectiveness and/or to detect or determine other factors relevant to delivering pacing therapy for disordered breathing.

A signal processor 320 may be used to condition the signals received from the electrodes 302, sensors 304 input devices 305, and/or information systems 306. The signal processor 320 may include, for example, drive circuitry for activating the sensors, as well as filters, amplifiers, and/or A/D conversion circuitry for conditioning the sensor signals.

The CRM device 300 may include a memory 360 used to store appropriate information and/or acquired data related to the monitoring, diagnosis and/or therapy delivery functions of the CRM device. The stored information and/or data may be periodically transferred to a remote device for further analysis and/or display.

The CRM device 300 may further include a disordered breathing (DB) detection/prediction unit 330 with components for detecting 332 and/or predicting 334 disordered breathing events. The DB detection/prediction unit 330 may acquire information related to the severity, duration, frequency and/or type of disordered breathing experienced by the patient. Control signals provided by the DB detection/prediction unit 330 to the cardiac therapy unit 340 may be used to adjust pacing therapy as described in more detail below. The pacing therapy may be adjusted based on detection of disordered breathing, predication of disordered breathing, severity, frequency, duration, and/or type of disordered breathing, or on other conditions related to disordered breathing.

In the embodiment illustrated in FIG. 3, the cardiac therapy unit 340 includes a pacemaker 342 that provides cardiac pacing therapy to one or more atria and/or one or more ventricles of the heart. The controller 343 controls the pacing therapy provided by the pacemaker. The controller 343 may initiate, modify or terminate the pacing therapy delivered by the pacemaker 342. The cardiac therapy unit 340 may further include an arrhythmia detector 344 to detect abnormal heart rhythms such as ventricular tachycardia or ventricular fibrillation. Upon detection of an abnormal rhythm, a defibrillator 346 may deliver a high energy electrical stimulation to the heart to terminate or mitigate the arrhythmia.

The CRM 300 may include a communications unit 380 for communicating with one or more separate devices, such as a device programmer 385, or other patient-external or patient-internal devices. Communication between cooperating devices allows the CRM 300 to provide information to separate devices that may be used for monitoring, diagnosis and/or therapy adjustment.

Figure 4:
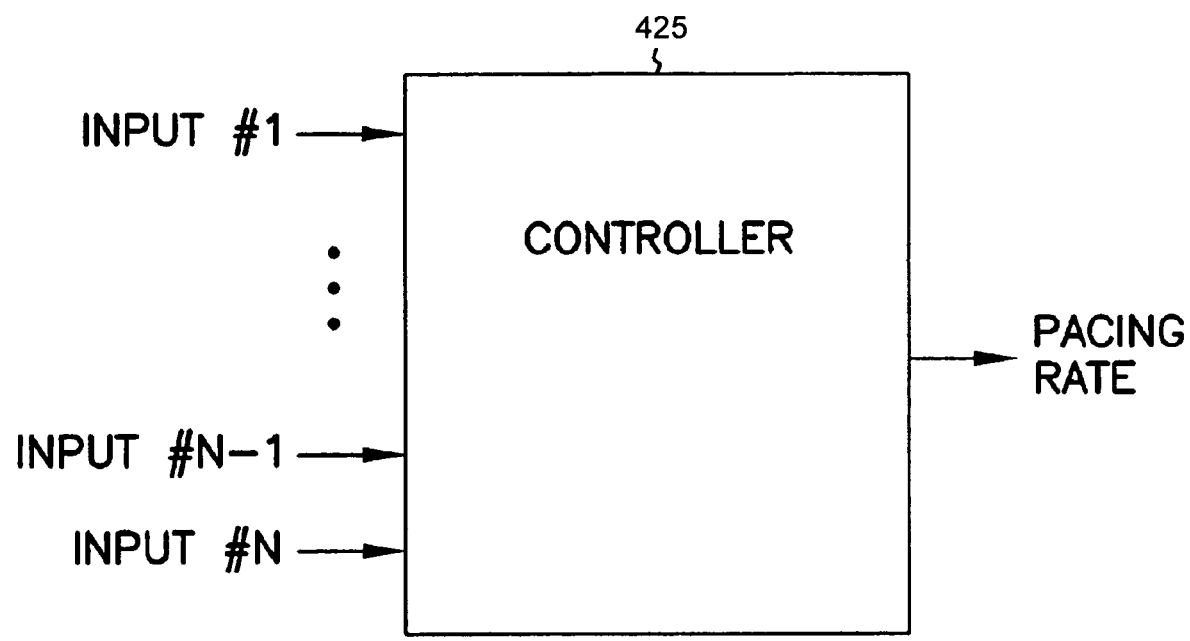
FIGS. 4 and 5 are block diagrams illustrating a controller configured to receive one or more inputs for modifying the rate at which cardiac pacing for disordered breathing is delivered in accordance with embodiments of the invention.

FIG. 4 is a block diagram illustrating a pacemaker controller 425 in accordance with embodiments of the invention. The pacemaker controller 425 uses signals from several different inputs to modify the rate at which pacing or other therapy is delivered. For example, Input #1 may provide information about atrial heart rate, Input #2 may provide information about ventricular heart rate, Input #3 may provide an accelerometer-based indication of activity, and Input #4 may provide an impedance-based indication of respiration, such as minute ventilation. Based on at least one of these and/or other inputs, controller 425 provides an output indication of pacing rate as a control signal delivered to a therapy delivery circuit, such as to one or more of an atrial therapy delivery circuit and a ventricular therapy delivery circuit.

Atrial and ventricular therapy delivery circuits issue pacing pulses based on one or more such control signals received from controller 425. Control of the pacing rate may be performed by controller 425, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device.

In various embodiments, a CRM device provides cardiac pacing therapy to treat disordered breathing. The CRM device obtains intervals between successive sensed or evoked atrial beats. The CRM device computes a new first indicated pacing interval based at least in part on the duration of a cardiac interval and a previous value of the first indicated pacing interval. In various implementations, the cardiac interval duration used to compute the new first indicated pacing interval may comprise a previous cardiac interval duration or a most recent cardiac interval duration. The CRM device provides pacing therapy delivered at a rate corresponding to the inverse of the duration of the first indicated pacing interval.

Figure 5:
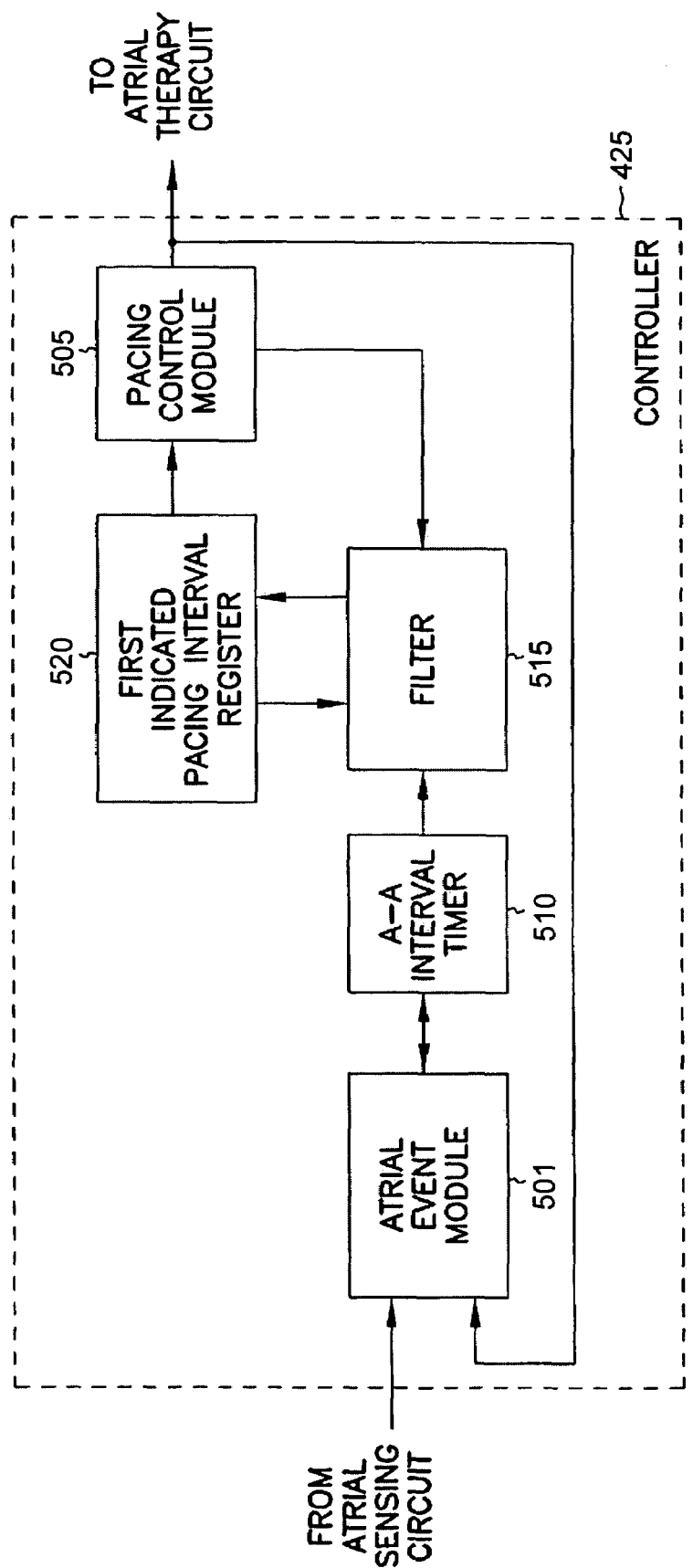

FIG. 5 is a block diagram illustrating one conceptualization of portions of the controller 425 used to effect overdrive pacing for disordered breathing therapy in accordance with embodiments of the invention. The description that follows involves atrial overdrive pacing in the AAI(R) or DDD(R) modes. It will be appreciated that similar techniques may be implemented to effect ventricular overdrive pacing in the VVI(R) mode or overdrive pacing in a biventricular mode.

At least one signal from an atrial sensing circuit is received by atrial event module 501, which recognizes the occurrence of atrial events included within the signal. Such events are also referred to as "beats," "activations," "depolarizations," "P-waves," or "contractions." Atrial event module 501 may detect intrinsic events (also referred to as sensed events) from the signal obtained from atrial sensing circuit. Atrial event module 501 may also detect evoked events (resulting from a pace) either from the signal obtained from atrial sensing circuit, or preferably from an atrial pacing control signal obtained from pacing control module 505, which also triggers the delivery of a pacing stimulus by atrial therapy circuit. Thus, atrial events include both intrinsic/sensed events and evoked/paced events.

A time interval between successive atrial events, referred to as an A-A interval, is recorded by a first timer, such as A-A interval timer 510. A filter 515 computes a "first indicated pacing interval," i.e., one indication of a desired time interval between atrial events or, stated differently, a desired atrial heart rate. The first indicated pacing interval is also referred to as an atrial pacing preference (APP) indicated pacing interval. In various embodiments, filter 515 includes an averager, a weighted averager, a median filter, an infinite impulse (IIR) filter, a finite impulse response (FIR) filter, or any other analog or digital signal processing circuit providing the desired signal processing described more particularly below.

In one embodiment, filter 515 computes a new value of the first indicated pacing interval (also referred to as the APP-indicated pacing interval) based on the duration of the most recent A-A interval recorded by timer 510 and on a previous value of the first indicated pacing interval stored in first indicated pacing interval register 520. Register 520 is then updated by storing the newly computed first indicated pacing interval in register 520. Based on the first indicated pacing interval stored in register 520, pacing control module 505 delivers control signals to atrial therapy circuit for delivering therapy, such as pacing stimuli, at the APP-indicated atrial heart rate corresponding to the inverse of the duration of the first indicated pacing interval.

Figure 6:
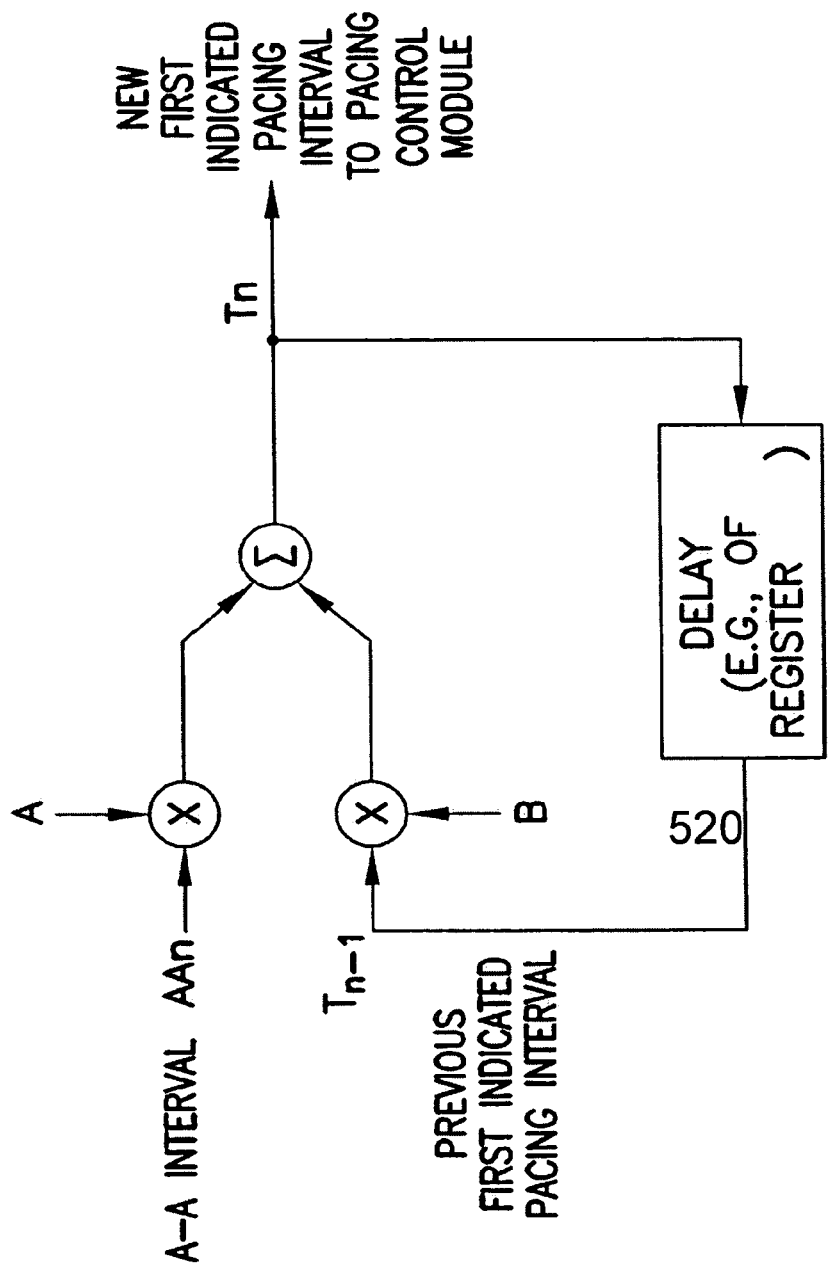
FIGS. 6-8 are signal flow diagrams illustrating pacing rate adjustment in accordance with embodiments of the invention.

FIG. 6 is a signal flow diagram illustrating one embodiment of operating filter 515. Upon the occurrence of a sensed or evoked atrial beat, timer 510 provides filter 515 with the duration of the A-A interval concluded by that beat, which is referred to as the most recent A-A interval ($AA_n$). Filter 515 also receives the previous value of the first indicated pacing interval ($T_{n-1}$) stored in register 520. The most recent A-A interval $AA_n$ and the previous value of the first indicated pacing interval $T_{n-1}$ are each scaled by respective constants A and B, and then summed to obtain a new value of the first indicated pacing interval ($T_n$), which is stored in register 520 and provided to pacing control module 505. In one embodiment, the coefficients A and B are different values, and are either programmable, variable, or constant.

If no atrial beat is sensed during the new first indicated pacing interval $T_n$, which is measured as the time from the occurrence of the atrial beat concluding the most recent A-A interval $AA_n$, then pacing control module 505 instructs atrial therapy circuit to deliver an atrial pacing pulse upon the expiration of the new first indicated pacing interval $T_n$. In one embodiment, operation of the filter is described by $T_n = A \bullet AA_n + B \cdot T_{n-1}$, where A and B are coefficients (also referred to as "weights"), $AA_n$ is the most recent A-A interval duration, and $T_{n-1}$ is the previous value of the first indicated pacing interval.

From these examples, it can be seen that the first indicated pacing interval can be calculated using either a sensed or paced terminating event and using either a sensed or paced initiating event.

Initialization of filter 515 includes seeding the filter by storing, in register 520, an initial interval value. In one embodiment, register 520 is initialized to an interval value corresponding to a lower rate limit (LRL), i.e., a minimum rate at which pacing pulses are delivered by device. Register 520 could alternatively be initialized with any other suitable value.

In one embodiment, operation of filter 515 is based on whether the beat concluding the most recent A-A interval $AA_n$ is a sensed/intrinsic beat or a paced/evoked beat. In this embodiment, the pacing control module 505, which controls the timing and delivery of pacing pulses, provides an input to filter 515 that indicates whether the most recent A-A interval $AA_n$ was concluded by an evoked beat initiated by a pacing stimulus delivered by CRM device, or was concluded by an intrinsic beat sensed by atrial sensing circuit.

In general terms, if the most recent A-A interval $AA_n$ is concluded by a sensed/intrinsic beat, then filter 515 provides a new first indicated pacing interval $T_n$ that is adjusted from the value of the previous first indicated pacing interval $T_{n-1}$. For example, the new first indicated pacing interval $T_n$ may be decreased by an amount that is based at least partially on the duration of the most recent A-A interval $AA_n$ and on the duration of the previous value of the first indicated pacing interval $T_{n-1}$. If, however, the most recent A-A interval $AA_n$ is concluded by a paced/evoked beat, then filter 515 may provide a new first indicated pacing interval $T_n$ that is increased from the value of the previous first indicated pacing interval $T_{n-1}$. For example, the new first indicated pacing interval $T_n$ may be increased by an amount that is based at least partially on the duration of the most recent A-A interval $AA_n$ and on the duration of the previous value of the first indicated pacing interval $T_{n-1}$. If no atrial beat is sensed during the new first indicated pacing interval $T_n$, measured as the time from the occurrence of the atrial beat concluding the most recent A-A interval $AA_n$, then pacing control module 505 may instruct the atrial therapy circuit to deliver an atrial pacing pulse upon the expiration of the new first indicated pacing interval $T_n$.

Figure 7:
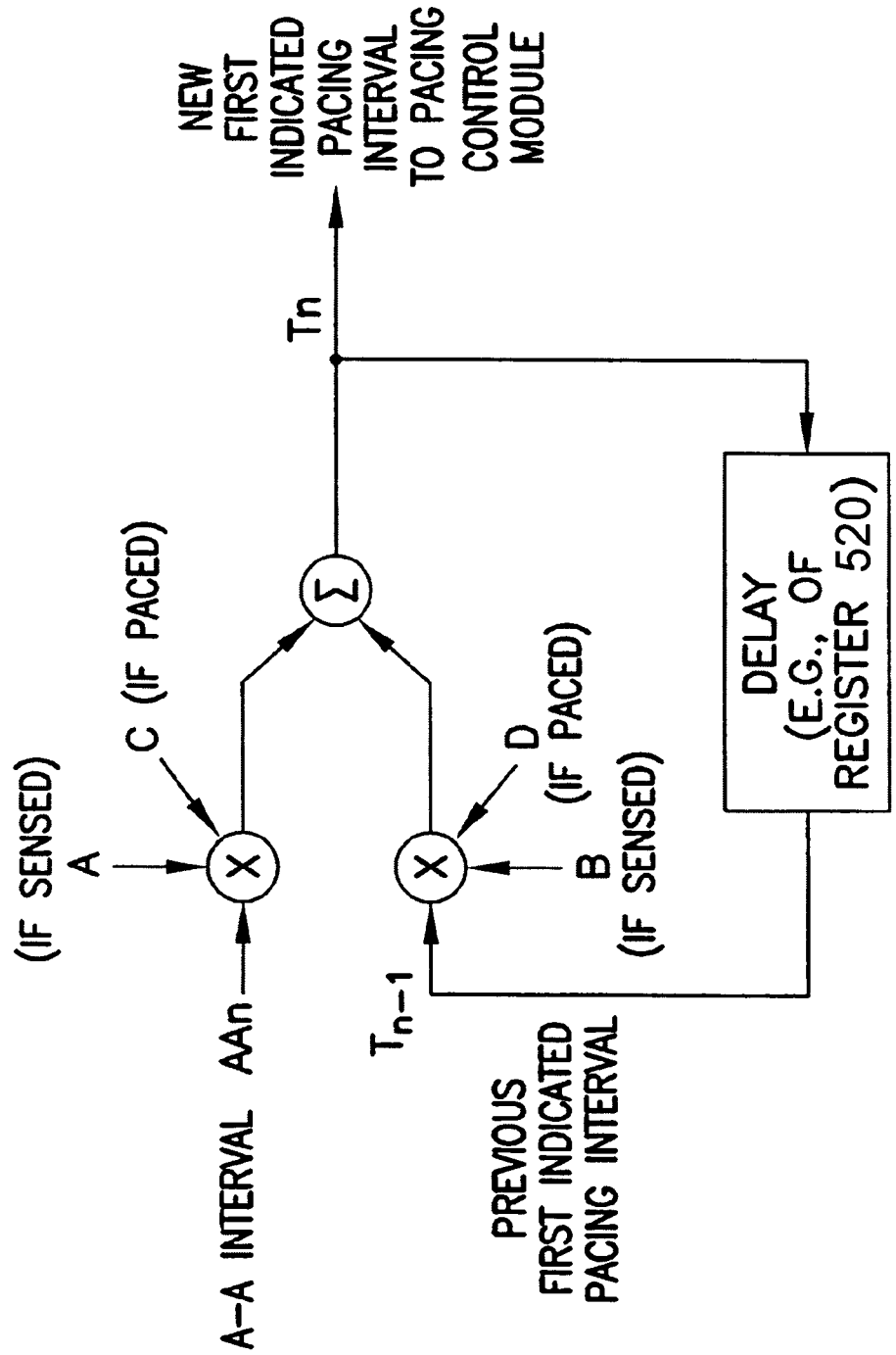

FIG. 7 is a signal flow diagram illustrating another conceptualization of operating filter 515, with certain differences from FIG. 6 more particularly described below. In this embodiment, the pacing control module 505, which controls the timing and delivery of pacing pulses, provides an input to filter 515 that indicates whether the most recent A-A interval $AA_n$ was concluded by an evoked beat initiated by a pacing stimulus delivered by the CRM device, or was concluded by an intrinsic beat sensed by a trial sensing circuit.

If the most recent A-A interval $AA_n$ was concluded by an intrinsic beat, then the most recent A-A interval, $AA_n$, and the previous value of the first indicated pacing interval, $T_{n-1}$, are each scaled by respective constants A and B, and then summed to obtain the new value of the first indicated pacing interval $T_n$, which is stored in register 520 and provided to pacing control module 505. Alternatively, if the most recent A-A interval $AA_n$ was concluded by an evoked/paced beat, then the most recent A-A interval $AA_n$ and the previous value of the first indicated pacing interval $T_{n-1}$ are each scaled by respective constants C and D, and then summed to obtain the new value of the first indicated pacing interval $T_n$, which is stored in register 520 and provided to pacing control module 505. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 515 is described by $T_n = A \cdot AA_n + B \cdot T_{n-1}$, if $AA_n$ is concluded by an intrinsic beat, and is described by $T_n = C \cdot AA_n + D \cdot T_{n-1}$, if $AA_n$ is concluded by a paced beat, where A, B, C and D are coefficients (also referred to as "weights"), $AA_n$ is the most recent A-A interval duration, $T_n$ is the new value of the first indicated pacing interval, and $T_{n-1}$ is the previous value of the first indicated pacing interval. If no atrial beat is sensed during the new first indicated pacing interval $T_n$, which is measured as the time from the occurrence of the atrial beat concluding the most recent A-A interval $AA_n$, then pacing control module 505 instructs atrial therapy circuit to deliver an atrial pacing pulse upon the expiration of the new first indicated pacing interval $T_n$.

Figure 8:
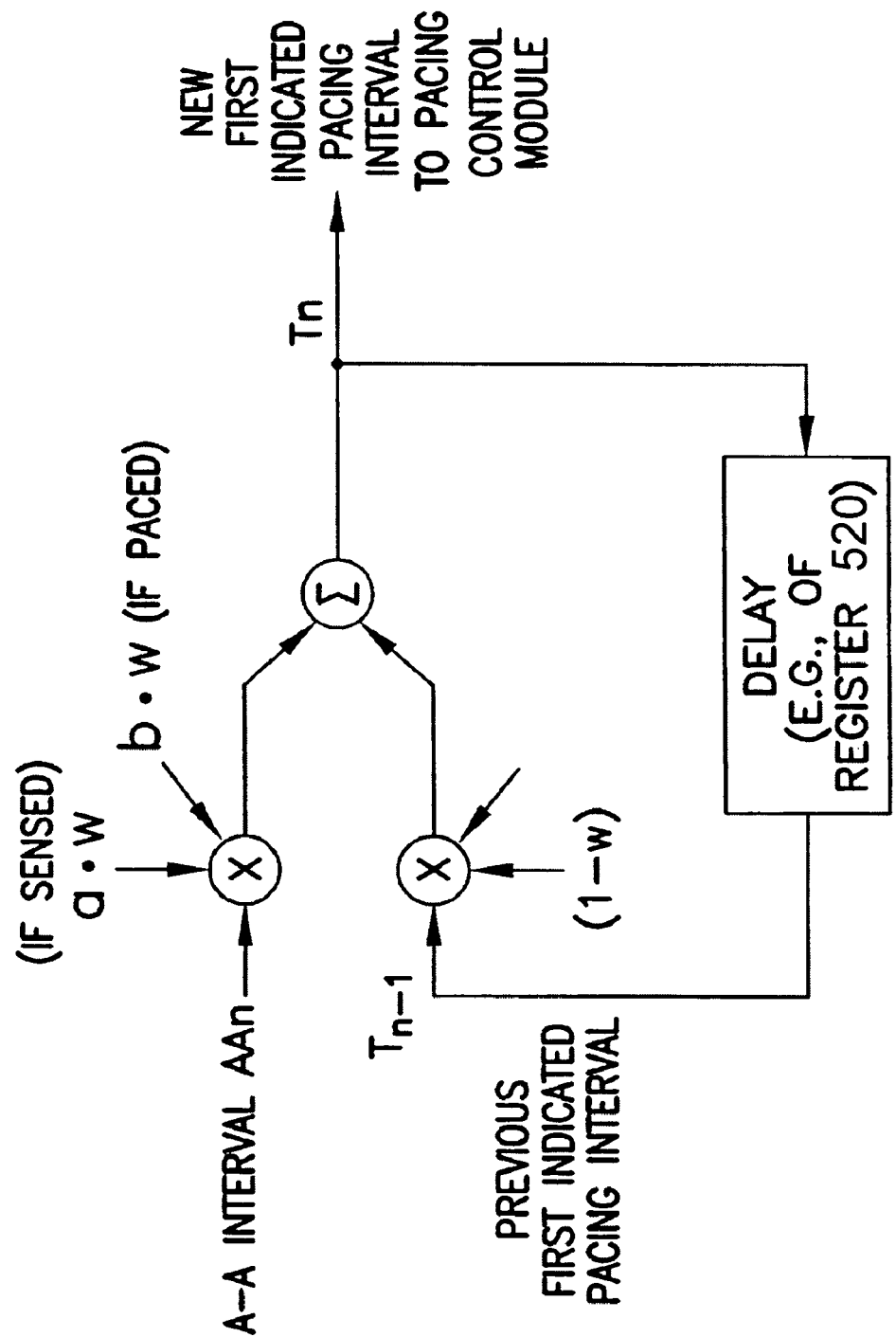

Another approach to operating filter 515 is illustrated in the signal flow graph of FIG. 8. In this embodiment, the coefficients A, B, C, and D can be more particularly described using an intrinsic coefficient (a), a paced coefficient (b), and a weighting coefficient (w). In one such embodiment, $A = a \cdot w$, $B = (1-w)$, $C = b \cdot w$, and $D = (1-w)$. In one example, operation of the filter 515 is described by $T_n = a \cdot w \cdot AA_n + (1-w) \cdot T_{n-1}$, if $AA_n$ is concluded by an intrinsic beat, otherwise is described by $T_n = b \cdot w \cdot AA_n + (1-w) \cdot T_{n-1}$, if $AA_n$ is concluded by a paced beat.

If no atrial beat is sensed during the new first indicated pacing interval $T_n$, which is measured as the time from the occurrence of the atrial beat concluding the most recent A-A interval $AA_n$, then pacing control module 505 instructs atrial therapy circuit to deliver an atrial pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $AA_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent A-A interval $AA_n$ increases and the weighting effect of the previous first indicated pacing rate $T_{n-1}$ decreases. In one embodiment, $w = \frac{1}{16} = 0.0625$. In another embodiment, $w = \frac{1}{32}$. Another possible range for w is from $w = \frac{1}{2}$ to $w = \frac{1}{1024}$. A further possible range for w is from about 0 to about 1. Other values of w, which need not include division by powers of two, may be substituted without departing from the present method and apparatus.

In one embodiment, intrinsic coefficient a, is selected to be less than (or, alternatively, less than or equal to) 1.0. In one example, the intrinsic coefficient a is selected to be lesser in value than the pacing coefficient b. In one embodiment, a may be about 0.6 and b may be about 1.5. In another embodiment, $a = 1.0$ and $b = 1.05$. One possible range for a is from $a = 0.6$ to $a = 1.0$, and for b is from $b = 1.05$ to $b = 1.5$. The coefficients may vary without departing from the present method and apparatus.

In one embodiment, for $a < 1.0$, filter 515 provides a new first indicated pacing interval $T_n$ that is at least slightly shorter than the expected intrinsic A-A interval being measured by timer 515. Thus, filter 515 operates to promote atrial pacing by increasing the APP-indicated rate until it becomes slightly faster than the intrinsic atrial rate. The APP-indicated rate is then gradually decreased to search for the underlying intrinsic atrial heart rate. After a sensed atrial beat, the APP filter 515 again increases the APP indicated pacing rate until it becomes faster than the intrinsic atrial rate by a small amount. As a result, most atrial heart beats are paced, rather than sensed.

The overdrive pacing as described above, or as implemented in connection with pacing one or more ventricles may be provided as therapy for disordered breathing. Additionally, such pacing therapy may be activated upon detection or prediction of disordered breathing. For example, pacing may occur at a programmed rate until a disordered breathing episode is detected. After detection of disordered breathing, the CRM device may switch to overdrive pacing to mitigate the disordered breathing.

In another example, the CRM may deliver pacing at a programmed rate until patient conditions indicate that disordered breathing is likely to occur. After disordered breathing is predicted, the CRM may deliver overdrive pacing to prevent or mitigate episodes of disordered breathing.

Although disordered breathing may occur while the patient is awake, it is most likely to occur during sleep. In another example, the CRM may be equipped with a sleep detection system. The CRM may switch from pacing at a programmed rate to overdrive pacing when the CRM detects that the patient is asleep or when the CRM detects a particular sleep state, e.g., non-REM sleep. Methods and systems for detecting sleep and various sleep states are described in U.S. patent application Ser. No. 10/309,771, filed Dec. 4, 2002, and U.S. patent application Ser. No. 10/643,006, filed Aug. 18, 2003, both of which are incorporated herein by reference.

Figure 9:
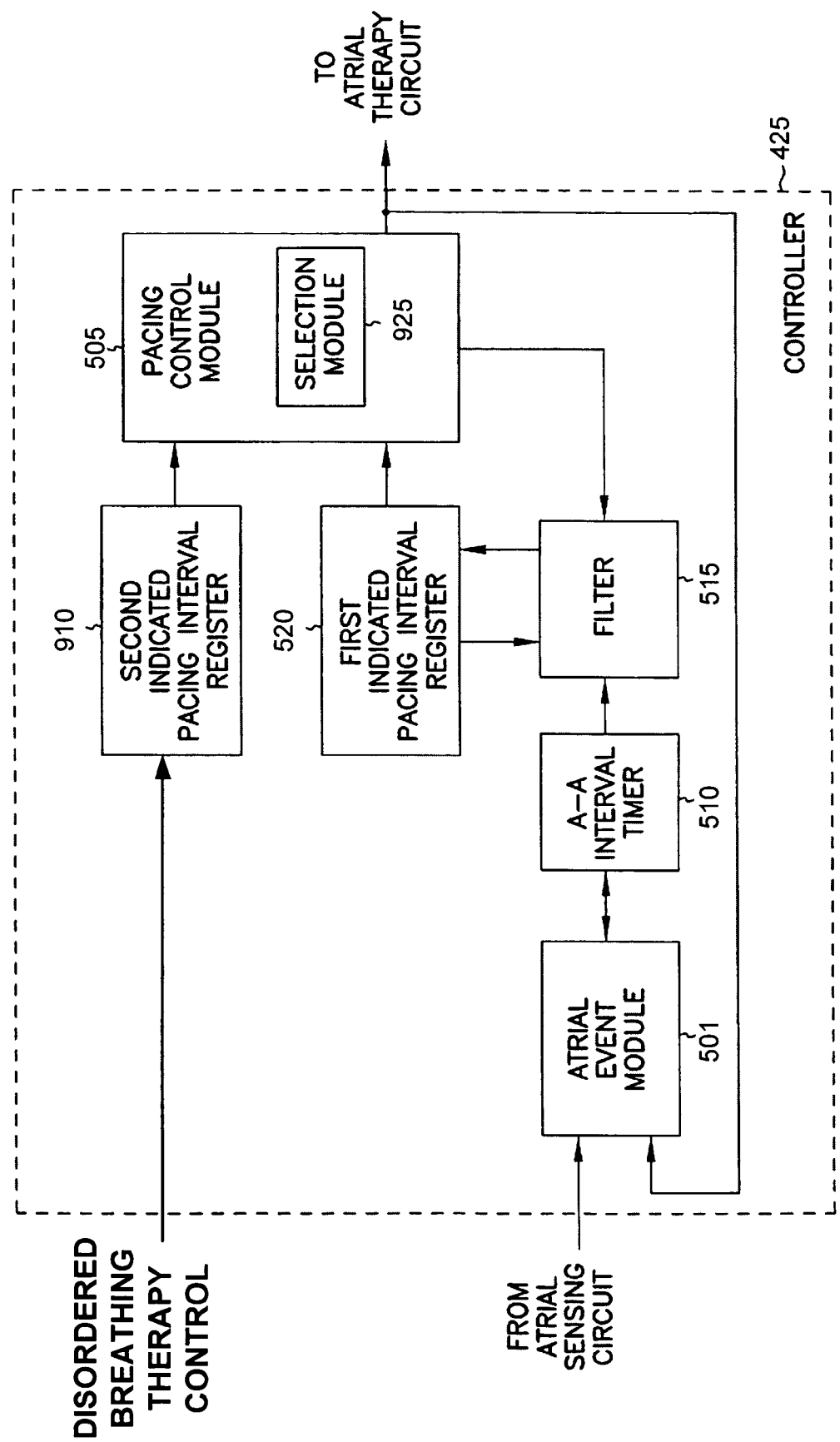
FIG. 9 is a block diagram illustrating a controller that includes several different inputs to modify the rate at which pacing or other therapy is delivered based on disordered breathing detection in accordance with embodiments of the invention.

FIG. 9 is a block diagram illustrating generally, by way of example, but not by way of limitation, another conceptualization of portions of controller 425, with certain differences from FIG. 5 more particularly described below. In FIG. 9, controller 425 receives from a disordered breathing therapy control circuit a control signal indicating an overdrive pacing rate for disordered breathing therapy. The signal may be based, for example, on the severity, duration, frequency or type of disordered breathing experienced by the patient, or by other factors, such as therapy interaction and/or patient comfort. In one example, the control signal may be based on a disordered breathing index, such as an apnea/hypopnea index. The disordered breathing therapy pacing rate is expressed in terms of a second indicated pacing interval stored in register 910. Methods and systems for determining various indices related to disordered breathing that may be useful in determining an impact of cardiac pacing on sleep quality and in providing cardiac pacing therapy for disordered breathing are described in commonly owned U.S. patent application Ser. No. 10/642,998, filed Aug. 18, 2003, which is incorporated herein by reference.

Pacing control module 905 delivers a control signal, which directs atrial therapy circuit to deliver a pacing pulse, based on either (or both) of the first or second indicated pacing intervals, stored in registers 920 and 910, respectively. In one embodiment, pacing control module 905 includes a selection module 915 that selects between the new first indicated pacing interval $T_n$ and the second indicated pacing interval that is modulated by disordered breathing conditions.

In one embodiment, selection module 925 selects the shorter of the first and second indicated pacing intervals as the selected indicated pacing interval $S_n$. If no atrial beat is sensed during the selected indicated pacing interval $S_n$, which is measured as the time from the occurrence of the atrial beat concluding the most recent A-A interval $AA_n$, then pacing control module 905 instructs atrial therapy circuit to deliver an atrial pacing pulse upon the expiration of the selected indicated pacing interval $S_n$.

In general terms, for this embodiment, the atrium is paced at the higher of the disordered breathing therapy rate and the APP-indicated rate. If, for example, the patient is experiencing no disordered breathing or only mild disordered breathing, the disordered breathing therapy rate is lower than the patient's intrinsic rate, then atrial pacing pulses will be delivered at the APP-indicated rate, which is typically slightly higher than the patient's intrinsic atrial heart rate. But if, for example, the patient is experiencing more significant disordered breathing, so that the disordered breathing therapy rate is higher than the APP-indicated rate, then pacing pulses generally will be delivered at the disordered breathing therapy rate. In an alternative embodiment, the pacing rate is determined by blending the disordered breathing therapy rate and the APP-indicated rate, rather than by selecting the higher of these two indicated rates (i.e., the shorter of the first and second indicated pacing intervals). In one such example, selection module 915 applies predetermined or other weights to the first and second indicated pacing intervals to compute the selected pacing interval Sn.

Figure 10:
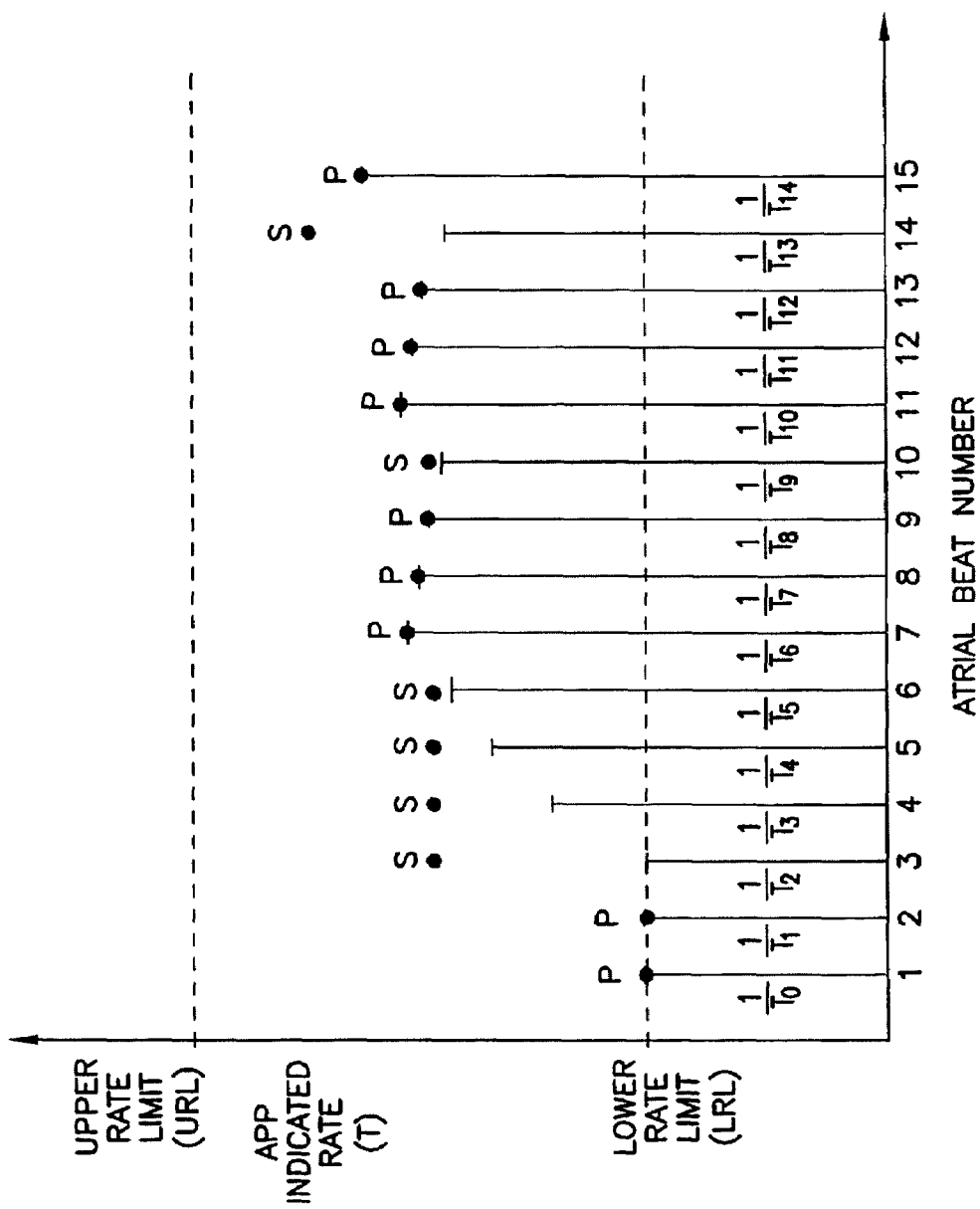
FIGS. 10 and 11 are graphs illustrating modification of a pacing rate in accordance with embodiments of the invention.

FIG. 10 is a graph illustrating generally, by way of example, but not by way of limitation, one embodiment of an APP-indicated rate for successive atrial heart beats for one mode of operating filter 515. As discussed above, the APP-indicated rate is simply the frequency, between atrial heart beats, associated with the first indicated pacing interval. Stated differently, the APP indicated rate is inversely related to the duration of the first indicated pacing interval. If pacing is based solely on the APP indicated rate, pacing control module 505 directs atrial therapy circuit to issue a pacing pulse after the time since the last atrial beat equals or exceeds the first indicated pacing interval. However, as described above, in certain embodiments, pacing control module 505 directs atrial therapy circuit to issue a pacing pulse based on factors other than the APP indicated rate such as for, example, based on the severity of disordered breathing experienced by the patient.

In the example illustrated in FIG. 10, a first paced atrial beat, indicated by a "P" was issued upon expiration of the first indicated pacing interval (i.e., the APP indicated pacing interval) $T_0$, as computed based on a previous atrial beat. In one embodiment, the new APP indicated pacing interval $T_1$ is computed based on the duration of most recent A-A interval $AA_1$ and a previous value of the APP indicated pacing interval $T_0$, as discussed above. In FIG. 10, the new APP indicated pacing interval $T_1$ corresponds to a lower rate limit (LRL) time interval. In one embodiment, as illustrated in FIG. 10, the allowable range of the APP indicated pacing interval is limited so that the APP indicated pacing interval does not exceed the duration of the LRL time interval, and so that the APP indicated pacing interval is not shorter than the duration of an upper rate limit (URL) time interval.

In the example of FIG. 10, the second atrial beat is also paced upon expiration of the APP indicated pacing interval $T_1$. In one embodiment, the new APP indicated pacing interval $T_2$ is computed based on the duration of most recent A-A interval $AA_2$ and a previous value of the APP indicated pacing interval, $T_1$, as discussed above. The first and second atrial beats are paced beats because the APP indicated atrial heart rate is higher than the underlying intrinsic atrial heart rate.

The third atrial beat is sensed well before expiration of the APP indicated pacing interval $T_2$, such that no pacing pulse is issued. For the sensed third atrial beat, filter 515 computes the new APP indicated pacing interval $T_3$ as being shorter in duration relative to the previous APP indicated pacing interval $T_2$.

The fourth, fifth, and sixth atrial beats are sensed before expiration of the APP indicated pacing interval $T_3$, $T_4$, and $T_5$, respectively. For each of the sensed fourth, fifth, and sixth atrial beats, filter 515 computes a new APP indicated pacing interval as being shorter in duration relative to the previous APP indicated pacing interval.

At the time of the seventh atrial beat, the APP indicated heart rate has increased above the underlying intrinsic atrial heart rate, such that the seventh atrial beat is paced upon expiration of the APP indicated pacing interval $T_6$. Because the seventh atrial beat is paced, rather than sensed, the new APP indicated pacing interval $T_7$ is computed as being longer than the previous APP indicated pacing interval $T_6$.

Similarly, the eighth and ninth atrial beats are each paced upon expiration of the corresponding APP indicated pacing interval, i.e., $T_7$, and $T_8$, respectively. Each APP indicated pacing interval $T_7$, and $T_8$ is longer than the corresponding previous APP indicated pacing interval, i.e., $T_6$, and $T_7$, respectively. In this way, the APP indicated atrial heart rate is gradually decreased to search for the underlying intrinsic atrial heart rate.

At the time of the tenth atrial beat, the APP indicated heart rate has been lowered sufficiently to allow the sensing of the tenth atrial beat. The tenth atrial beat is sensed before expiration of the APP indicated pacing interval $T_9$, such that no pacing pulse is issued. For the sensed tenth atrial beat, filter 515 computes the new APP indicated pacing interval $T_{10}$ as being shorter in duration relative to the previous APP indicated pacing interval $T_9$.

The eleventh atrial beat is paced upon expiration of the APP indicated pacing interval $T_{10}$. For the paced eleventh atrial beat, filter 515 computes the new APP indicated pacing interval $T_{11}$ as being longer in duration relative to the previous APP indicated pacing interval $T_{10}$. Similarly, the twelfth and thirteenth atrial beats are each paced upon expiration of the corresponding APP indicated pacing interval, i.e., $T_{11}$, and $T_{12}$, respectively. Each APP indicated pacing interval $T_{12}$, and $T_{13}$ is longer than the corresponding previous APP indicated pacing interval, i.e., $T_{11}$, and $T_{12}$, respectively. In this way, the APP indicated atrial heart rate is gradually decreased to find the underlying intrinsic atrial heart rate.

The fourteenth atrial beat is sensed before expiration of the APP indicated pacing interval $T_{13}$, such that no pacing pulse is issued. For the sensed fourteenth atrial beat, filter 515 computes the new APP indicated pacing interval $T_{14}$ as being shorter in duration relative to the previous APP indicated pacing interval $T_{13}$.

The fifteenth atrial beat is paced upon expiration of the APP indicated pacing interval $T_{14}$. For the paced fifteenth atrial beat, filter 515 computes the new APP indicated pacing interval $T_{15}$ as being longer in duration relative to the previous APP indicated pacing interval $T_{14}$.

The intrinsic coefficient a of filter 515 controls the "attack slope" of the APP indicated heart rate as the APP indicated heart rate increases because of sensed intrinsic beats. The paced coefficient b of filter 515 controls the "decay slope" of the APP indicated heart rate as the APP indicated heart rate decreases during periods of paced beats. In one embodiment, in which a<1.0 and b>1.0, decreasing the value of a further beneath 1.0 increases the attack slope such that the APP indicated rate increases faster in response to sensed intrinsic beats, while decreasing the value of b toward 1.0 decreases the decay slope such that the APP indicated rate decreases more slowly during periods of paced beats. Conversely, for a<1.0 and b>1.0, increasing the value of a toward 1.0 decreases the attack slope such that the APP indicated rate increases more slowly in response to sensed intrinsic beats, while increasing the value of b from 1.0 increases the decay slope such that the APP indicated rate decreases more quickly during periods of paced beats.

In one embodiment, for a<1.0 and b>1.0, decreasing both a and b increases the APP indicated rate such that the APP indicated rate is higher above the mean intrinsic rate. Because the APP indicated rate is higher, variability in the intrinsic heart rate is less likely to result in sensed events. On the other hand, for a<1.0 and b>1.0, increasing both a and b decreases the APP indicated rate such that it is closer to, the mean intrinsic rate. Because the APP indicated rate is closer to the mean intrinsic rate, the same degree of variability in the intrinsic heart rate is more likely to result in sensed events. Thus, by adjusting the coefficients of filter 515, as discussed above, it is possible to obtain more intrinsic beats than paced beats for a particular degree of variability in the patient's heart rate.

In one embodiment, these coefficients are programmable by the user, such as by using remote programmer. In another embodiment, the user selects a desired performance parameter (e.g., desired degree of overdrive pacing, desired attack slope, desired decay slope, etc.) from a corresponding range of possible values, and CRM device automatically selects the appropriate combination of coefficients of filter 515 to provide a filter setting that corresponds to the selected user-programmed performance parameter, as illustrated generally by Table 5. Other levels of programmability or different combinations of coefficients may also be used.

TABLE 5

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Aggressive Attack/Decay) | 1.0 | 1.05 |
| 2 | 0.9 | 1.2 |
| 3 | 0.8 | 1.3 |
| 4 | 0.7 | 1.4 |
| 5 (More Aggressive Attack/Decay) | 0.6 | 1.5 |

FIG. 10 illustrates that sensed atrial beats increase the APP indicated rate by an amount that is based on the sensed atrial heart rate. Thus, for an abrupt and large increase in sensed atrial rate, the APP indicated rate will increase faster than for a slower and smaller increase in sensed atrial heart rate. However, increases in the APP indicated rate do not depend solely on the sensed atrial heart rate. Instead, such increases in the APP indicated heart rate also depend on the previous value of the APP indicated heart rate. This provides a smoothing function so that the APP indicated heart rate is not overly sensitive to a single extremely premature atrial beat, changes in the atrial rate are more gradual, and the degree of such rate changes is programmably adjustable, as described above. Moreover, in one embodiment, filter 515 operates continuously to provide continuous rate adjustment based on the APP indicated rate.

Figure 11:
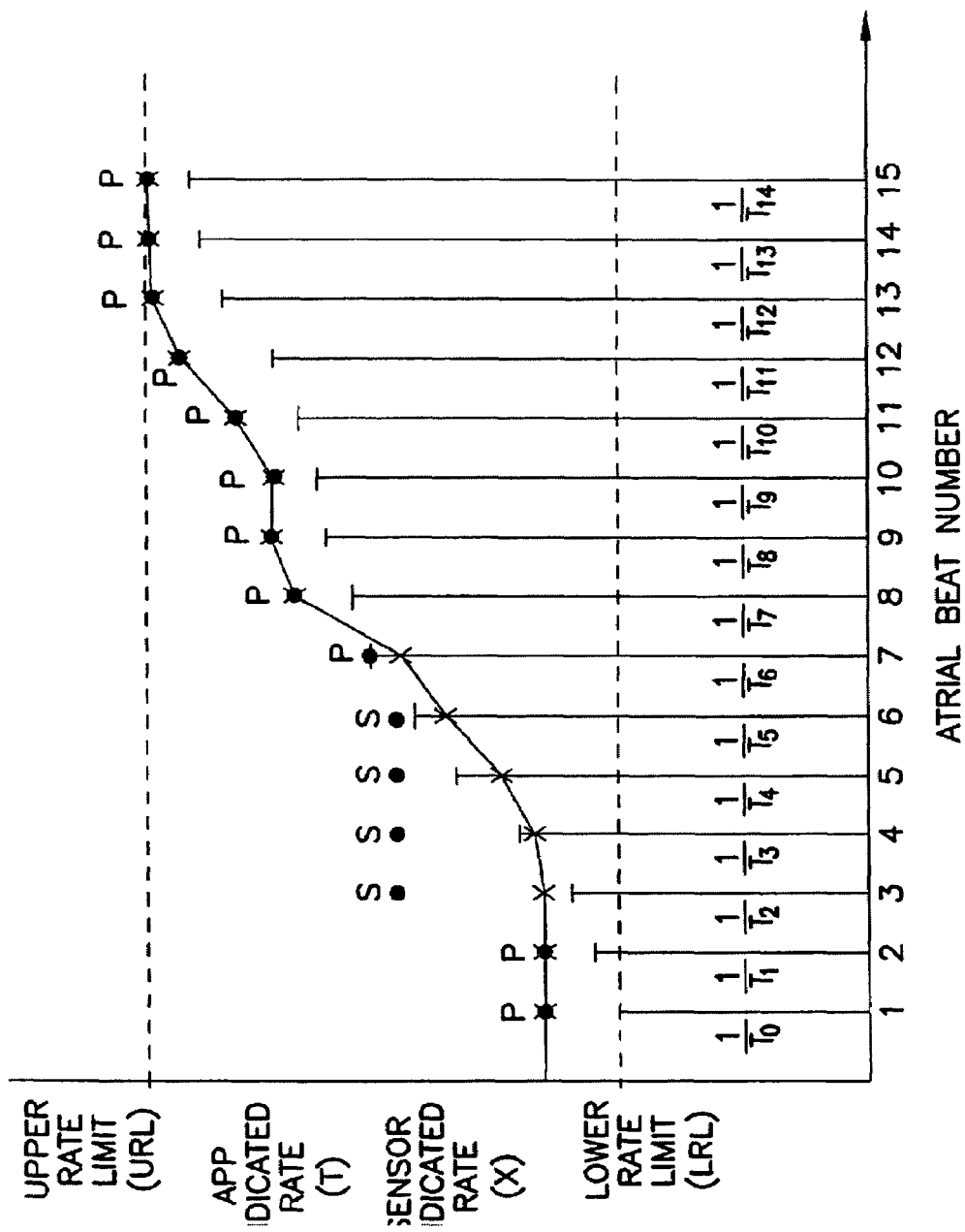

FIG. 11 is a graph illustrating generally, by way of example, but not by way of limitation, one embodiment of selecting between more than one indicated pacing interval. FIG. 11 is similar to FIG. 10 in some respects, but FIG. 11 includes a second indicated pacing interval. In one embodiment, the first indicated pacing interval is the APP indicated pacing interval, described above, and the second indicated pacing interval is a disordered breathing therapy pacing interval, based on the severity, frequency, duration, type, or other parameter of disordered breathing experienced by the patient.

In one embodiment, a selected indicated pacing interval is based on the shorter of the first and second indicated pacing intervals. Stated differently, CRM device provides pacing pulses at the higher indicated pacing rate. In the example illustrated in FIG. 11, the first and second beats and the eighth through fifteenth beats are paced at the disordered breathing therapy indicated rate, because it is higher than the APP indicated atrial rate and the intrinsic (sensed) atrial rate. The third, fourth, fifth and sixth atrial beats are sensed intrinsic beats that are sensed during the shorter of either of the APP and sensor indicated pacing intervals. The seventh beat is paced at the APP indicated rate, because it is higher than the disordered breathing therapy indicated rate, and because no intrinsic beat is sensed during the APP indicated interval $T_6$. In this embodiment, the ranges of both the sensor indicated rate and the APP indicated rate are limited so that they do not extend to rates higher than the URL or to rates lower than the LRL. In one embodiment, the above-described equations for filter 515 operate to increase the APP indicated rate toward the disordered breathing therapy indicated rate when the sensor indicated rate is greater than the APP indicated rate, as illustrated by first through third and eighth through fifteenth beats in FIG. 11.

In an alternate embodiment, however, $T_n = b \cdot w \cdot AA_n + (1-w) \cdot T_{n-1}$, if $AA_n$ is concluded by a APP indicated paced beat, and $T_n = T_{n-1}$ if $AA_n$ is concluded by a disordered breathing therapy indicated paced beat, thereby leaving the APP indicated rate unchanged for disordered breathing therapy indicated paced beats. In one embodiment, the LRL and the URL are programmable by the user, such as by using remote programmer.

In one embodiment, filter 515 includes variable coefficients such as, for example, coefficients that are a function of heart rate (or its corresponding time interval). In one example, operation of the filter 515 is described by $T_n = a \cdot w \cdot AA_n + (1-w) \cdot T_{n-1}$ if $AA_n$ is concluded by an intrinsic beat, otherwise is described by $T_n = b \cdot w \cdot AA_n + (1-w) \cdot T_{n-1}$, if $AA_n$ is concluded by a paced beat, where at least one of a and b are linear, piecewise linear, or nonlinear functions of one or more previous A-A intervals such as, for example, the most recent A-A interval, $AA_n$.

Figure 12:
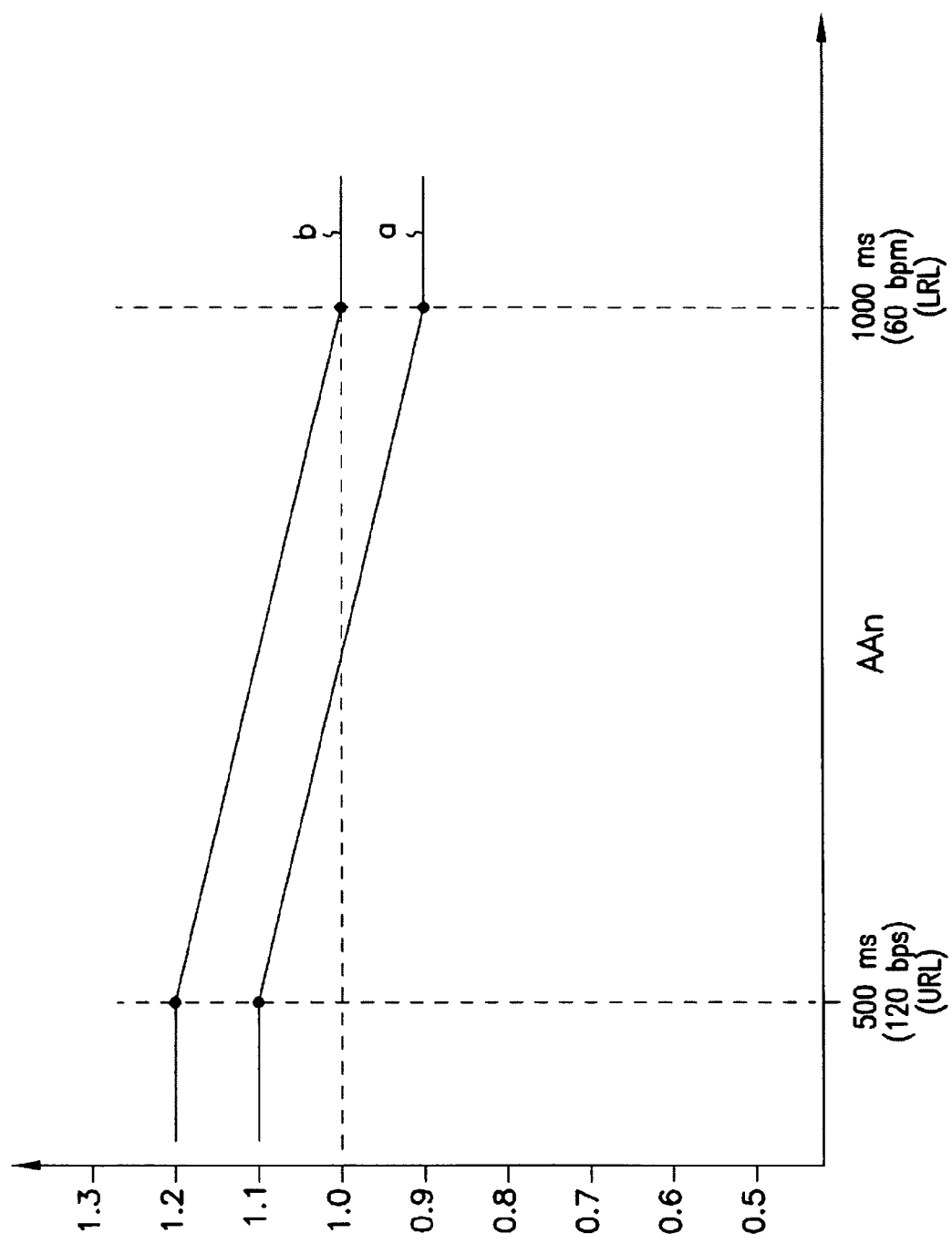
FIG. 12 is a graph illustrating a method of using at least one of coefficients a and b as a function of one or more previous cardiac intervals in accordance with embodiments of the invention.

FIG. 12 is a graph illustrating generally, by way of example, but not by way of limitation, one embodiment of using at least one of coefficients a and b as a function of one or more previous A-A intervals such as, for example, the most recent A-A interval, $AA_n$. In one such example, a is less than 1.0 when $AA_n$ is at or near the lower rate limit (e.g., 1000 millisecond interval or 60 beats/minute), and a is greater than 1.0 when $AA_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $AA_n$ is at or near the lower rate limit, and b is greater than 1.0 when $AA_n$ is at or near the upper rate limit. For a constant a, using a smaller value of b at lower rates will decrease the pacing rate more slowly for paced events; using a larger value of b at higher rates decreases pacing rate more quickly for paced events.

The above-described system provides, among other things, a cardiac rhythm management system including an atrial pacing preference (APP) filter for promoting atrial pacing. The APP filter controls the timing of delivery of atrial pacing pulses. The atrial pacing preference pacing may be initiated upon detection or prediction of disordered breathing, for example, to provide overdrive pacing to terminate or mitigate occurrences of disordered breathing.

The atrial pacing pulses are delivered at a first indicated pacing rate, i.e., the APP-indicated rate, that is typically at a small amount above the intrinsic atrial heart rate. For sensed beats, the APP indicated pacing rate is increased until it becomes slightly faster than the intrinsic atrial heart rate. The APP-indicated pacing rate is then gradually decreased to search for the underlying intrinsic atrial heart rate. Then, after a sensed atrial beat, the APP filter again increases the APP indicated pacing rate until it becomes faster than the intrinsic atrial rate by a small amount. As a result, most atrial heart beats are paced, rather than sensed.

Although the preceding discussion contemplates providing atrial overdrive pacing for disordered breathing therapy, similar processes for providing ventricular overdrive pacing or bi-ventricular overdrive pacing may be implemented. The pacing rate may be adjusted based on characteristics of the disordered breathing experienced by the patient. For example, the overdrive pacing may be modulated by the type, severity, frequency, and/or duration of the disordered breathing.

Further, the smoothed pacing rate may be limited. For example, the pacing rate may be capped or limited before therapy is delivered. In another implementation, the intrinsic input interval may be limited to some predetermined value. The predetermined may be set by the physician or may be determined from other variables. By limiting the input intrinsic interval, the output pacing rate is limited. Limiting the smoothed pacing rate may be useful in managing atrial fibrillation or flutter, for example.

Methods and systems for providing rate regularization for atrial and ventricular pacing that may be used to implement disordered breathing therapy in accordance with embodiments of the present invention are described in commonly owned U.S. Pat. Nos. 6,351,669, 6,353,759, and 6,285,907, which are incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for delivering disordered breathing therapy to a patient, comprising:
   measuring cardiac intervals between cardiac beats;
   computing a first indicated pacing interval based at least on a measured cardiac interval duration and a previous value of the first indicated pacing interval; and
   providing cardiac pacing to mitigate disordered breathing based on the first indicated pacing interval.

2. The method of claim 1, further comprising initiating delivery of the disordered breathing therapy based on detection of disordered breathing.

3. The method of claim 1, further comprising initiating delivery of the disordered breathing therapy based on prediction of disordered breathing.

4. The method of claim 1, wherein:
   obtaining cardiac intervals comprises obtaining intervals between ventricular beats; and
   providing the cardiac pacing to mitigate the disordered breathing comprises providing ventricular pacing.

5. The method of claim 1, wherein:
   obtaining the cardiac intervals comprises obtaining intervals between atrial beats; and
   providing the cardiac pacing to mitigate the disordered breathing comprises providing atrial pacing.

6. The method of claim 1, further comprising adapting the cardiac pacing based on characteristics of the disordered breathing.

7. The method of claim 1, further comprising adapting the cardiac pacing based on therapy efficacy.

8. The method of claim 1, further comprising adapting the cardiac pacing based on an impact of the therapy on the patient.

9. The method of claim 1, wherein the cardiac interval duration comprises a most recent cardiac interval duration.

10. The method of claim 1, wherein the cardiac interval duration comprises previous cardiac interval duration.

11. The method of claim 1, wherein providing the cardiac pacing to mitigate the disordered breathing comprises providing atrial pacing.

12. The method of claim 1, wherein providing the cardiac pacing to mitigate the disordered breathing comprises providing ventricular pacing.

13. The method of claim 1, wherein providing the cardiac pacing to mitigate the disordered breathing comprises providing bi-ventricular pacing.

14. The method of claim 1, wherein providing the cardiac pacing to mitigate the disordered breathing comprises providing overdrive pacing.

15. The method of claim 1, wherein providing the cardiac pacing to mitigate the disordered breathing comprises pacing at a rate above an intrinsic rate.

16. The method of claim 1, wherein measuring the cardiac intervals comprises measuring each cardiac interval duration between successive cardiac events beginning from an initiating event comprising a sensed or paced cardiac beat.

17. The method of claim 1, wherein measuring the cardiac intervals comprises measuring each cardiac interval duration between successive cardiac events from an initiating event to a terminating event comprising a sensed cardiac beat.

18. The method of claim 1, wherein computing the first indicated pacing interval comprises combining the previous value of the first indicated pacing interval and the measured cardiac interval duration.

19. The method of claim 1, wherein computing the first indicated pacing interval comprises combining the previous value of the first indicated pacing interval and the measured cardiac interval duration using a recursive filter.

20. A system for providing disordered breathing therapy to a patient, comprising:
 a circuit configured to detect cardiac beats and measure cardiac intervals between cardiac beats;
 a controller coupled to the circuit and configured to compute a first indicated pacing interval based at least on a measured cardiac interval duration and a previous value of the first indicated pacing interval; and
 a cardiac pacing circuit coupled to the controller and configured to provide cardiac pacing to mitigate disordered breathing based on the first indicated pacing interval.

21. The therapy system of claim 20, wherein the controller comprises
 a timer configured to measure durations of the cardiac intervals.

22. The therapy system of claim 20, wherein the controller comprises:
 a timer configured to measure durations of the cardiac intervals between successive cardiac beats; and
 a filter configured to combine the previous value of the first indicated pacing interval and the measured cardiac interval duration.

23. The therapy system of claim 20, further comprising disordered breathing detection circuitry coupled to the controller and configured to detect disordered breathing and initiate therapy to mitigate the disordered breathing based on the detection of disordered breathing.

24. The therapy system of claim 20, further comprising a detection system coupled to the controller, the detection system configured to detect one more characteristics of the disordered breathing, wherein the controller is further configured to adjust the cardiac pacing based on the one or more disordered breathing characteristics.

25. The therapy system of claim 20, further comprising a detection system coupled to the controller, the detection system configured to detect an impact of the disordered breathing therapy on the patient, wherein the controller is further configured to adjust the cardiac pacing based on the impact of the disordered breathing therapy on the patient.

26. The therapy system of claim 20, further comprising a disordered breathing prediction unit coupled to the controller and configured to detect disordered breathing and initiate therapy to mitigate the disordered breathing based on the prediction of disordered breathing.

27. The therapy system of claim 20, wherein the cardiac pacing circuit is configured to pace one or more atria.

28. The therapy system of claim 20, wherein the cardiac pacing circuit is configured to pace one or more ventricles.

29. The therapy system of claim 20, wherein the cardiac interval duration comprises a previous cardiac interval duration.

30. The therapy system of claim 20, wherein the cardiac interval duration comprises a most recent cardiac interval duration.

31. A system for providing disordered breathing therapy, comprising:
 means for measureing cardiac intervals between cardiac beats;
 means for computing a first indicated pacing interval based at least on a cardiac interval duration and a previous value of the first indicated pacing interval; and
 means for providing cardiac pacing to mitigate disordered breathing based at least on the first indicated pacing interval.

32. The system of claim 31, further comprising means for initiating the disordered breathing therapy based on detection of disordered breathing.

33. The system of claim 31, further comprising means for initiating the disordered breathing therapy based on prediction of disordered breathing.

34. The system of claim 31, further comprising means for adapting the cardiac pacing based on characteristics of the disordered breathing.

35. The system of claim 31, further comprising means for adapting the cardiac pacing based on therapy efficacy.

36. The system of claim 31, further comprising means for adapting the cardiac pacing based on an impact of the therapy on the patient.

* * * * *

UNITED STATES PATENT AND TRADEMARK OFFICE
CERTIFICATE OF CORRECTION

PATENT NO. : 7,336,996 B2
APPLICATION NO. : 10/798794
DATED : February 26, 2008
INVENTOR(S) : Hartley et al.

Page 1 of 1

It is certified that error appears in the above-identified patent and that said Letters Patent is hereby corrected as shown below:

<u>In the References Cited, U.S. Patent Documents:</u>

On page 2, line 35: "6,276,727 B1" should read --6,275,727 B1--.

Col. 8, line 28: "$T_n = A \cdot AA_n + B \cdot\cdot T_{n-1}$," should read --$T_n = A \cdot AA_n + B \cdot T_{n-1}$,--.

Signed and Sealed this

Eighth Day of July, 2008

JON W. DUDAS
*Director of the United States Patent and Trademark Office*